(12) United States Patent  
Couture et al.

(10) Patent No.: US 11,602,358 B2  
(45) Date of Patent: Mar. 14, 2023

(54) ROBOTIC SURGERY PLANAR CUTTING SYSTEMS AND METHODS

(71) Applicant: ORTHOSOFT ULC, Montreal (CA)

(72) Inventors: Pierre Couture, Montreal (CA); Louis-Philippe Amiot, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 256 days.

(21) Appl. No.: 17/091,015

(22) Filed: Nov. 6, 2020

(65) Prior Publication Data

US 2021/0052288 A1 Feb. 25, 2021

Related U.S. Application Data

(63) Continuation of application No. 16/265,318, filed on Feb. 1, 2019, now Pat. No. 10,856,890.

(60) Provisional application No. 62/625,556, filed on Feb. 2, 2018.

(51) Int. Cl.
| | |
|---|---|
| *A61B 17/16* | (2006.01) |
| *A61B 34/30* | (2016.01) |
| *A61B 90/50* | (2016.01) |
| *A61F 2/46* | (2006.01) |
| *A61B 17/00* | (2006.01) |
| *A61B 34/20* | (2016.01) |

(52) U.S. Cl.  
CPC ...... *A61B 17/1626* (2013.01); *A61B 17/1628* (2013.01); *A61B 17/1659* (2013.01); *A61B 17/1675* (2013.01); *A61B 34/30* (2016.02); *A61B 90/50* (2016.02); *A61F 2/461* (2013.01); *A61B 2017/00477* (2013.01); *A61B 2017/1602* (2013.01); *A61B 2034/2055* (2016.02)

(58) Field of Classification Search  
CPC .................... A61B 17/1659; A61B 17/1626  
See application file for complete search history.

(56) References Cited

U.S. PATENT DOCUMENTS

| | | | |
|---|---|---|---|
| 6,325,808 B1 * | 12/2001 | Bernard | A61B 34/30 606/139 |
| 2010/0145343 A1 * | 6/2010 | Johnson | A61B 17/1624 606/85 |
| 2014/0276838 A1 * | 9/2014 | Tsukayama | G05G 1/04 74/491 |
| 2015/0039037 A1 * | 2/2015 | Donner | A61B 17/1604 606/85 |
| 2017/0135733 A1 * | 5/2017 | Donner | A61B 17/7049 |

(Continued)

*Primary Examiner* — Christian A Sevilla  
(74) *Attorney, Agent, or Firm* — Norton Rose Fulbright Canada LLP

(57) ABSTRACT

Examples of robotically controlled planar cutting systems and methods for controlling cutting systems to prepare bone tissue in surgical procedures, are generally described herein. Applicable surgical procedures for the robotically controlled cutting systems and methods include procedures involving the preparation (e.g., removal, surfacing) of bone tissue, such as is performed in knee arthroplasties.

In an example, a robotically controlled planar cutting system can include a housing, a cutting element disposed in the housing, and a cutting control mechanism in communication with a robotic controller to control operation of the cutting element to machine a planar surface. The cutting element can be exposed and retracted relative to the housing and can include a plurality of cutting implements arranged to machine the planar surface.

13 Claims, 13 Drawing Sheets

(56) References Cited

U.S. PATENT DOCUMENTS

| | | | |
|---|---|---|---|
| 2018/0177523 A1* | 6/2018 | Piron | A61B 5/0062 |
| 2018/0214168 A1* | 8/2018 | Overmyer | A61B 17/32 |
| 2019/0090968 A1* | 3/2019 | Swarup | A61B 34/37 |
| 2019/0125361 A1* | 5/2019 | Shelton, IV | A61B 90/30 |
| 2019/0192239 A1* | 6/2019 | Xu | A61B 17/00234 |
| 2019/0254755 A1* | 8/2019 | Bonutti | A61B 90/37 |

* cited by examiner

ROBOTIC SURGERY PLANAR CUTTING SYSTEMS AND METHODS

RELATED APPLICATION

The present application is a continuation of U.S. Non-Provisional application Ser. No. 16/265,318 filed on Feb. 1, 2019 which claims priority on U.S. Provisional Application Ser. No. 62/625,556, filed on Feb. 2, 2018, and incorporated herewith by reference.

TECHNICAL FIELD

This disclosure is generally related to tools and methods for removing bone during a surgical procedure. In particular, the tools and methods described herein can be used to prepare a bone surface during a total knee arthroplasty.

BACKGROUND

The use of robotics in surgery is on the rise. Knee arthroplasty surgeries are performed over half a million times a year in the United States. In some cases, the surgeries are performed with assistance from a surgical robot.

Surgical robots can be outfitted with cutting tools for preparing a bone surface. In some surgeries, bone tissue must be prepared to receive an implant having a specified geometry. Preparing the bone tissue can include removing a portion of the bone tissue in order to modify the bone surface shape and make room for the implant.

SUMMARY

Therefore, in accordance with the present disclosure, there is provided a robotically controlled planar cutting system, the planar cutting system comprising: a housing including a superior surface and an inferior surface; a cutting element disposed within the housing, wherein the cutting element is exposable through the superior surface and is populated with at least one cutting implement configured for machining a planar surface; and a cutting control mechanism configured for being in communication with a robotic controller to control the operation of the cutting element to machine the planar surface.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As discussed above, surgical robots can be outfitted with cutting tools for preparing a bone surface. In some surgeries, bone tissue is prepared to receive an implant having a specified geometry. Preparing the bone tissue can include removing a portion of the bone tissue in order to modify the bone surface shape.

During a knee arthroplasty, e.g., a total knee arthroplasty, it can be difficult to prepare (e.g., cut) a planar bone surface to receive an implant. Current surgical robots and cutting systems are limited in their ability to machine a planar bone surface to match the implant surface to be received. Moreover, it is often desired that surgery be as minimally invasive as possible. Yet, cutting planar bone may often involve lateal and axial access to the bone, which may involve relative large incisions in soft tissue.

Systems and methods for preparing a bone surface during an orthopedic knee procedure and for performing the procedure are described herein. The systems and methods can assist in planar surface preparation, and may reduce surgical time.

While some examples are described with reference to total knee arthroplasty, many of the techniques described herein can be used with other orthopedic implant procedures.

Figure 1:
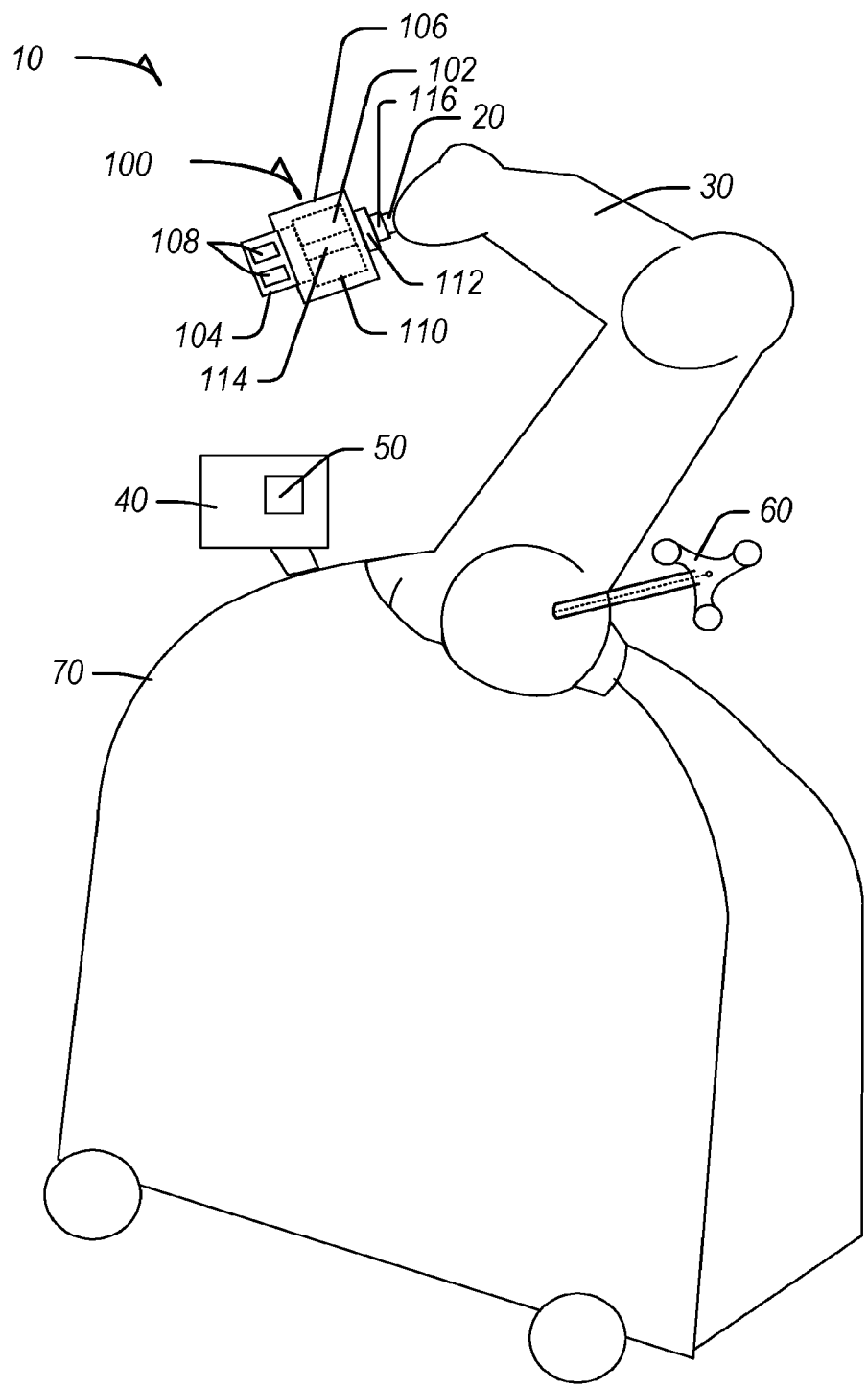
FIG. 1 illustrates a surgical robot having a cutting system coupled to an end effector, in accordance with at least one example.

FIG. 1 illustrates a surgical robot 10 having a cutting system 100 coupled to an end effector 20, in accordance with at least one example. The surgical robot 10 can be a robotic arm 30, and can include a user interface 40, a robotic controller 50, and a tracking system 60 operably coupled to one another. In some examples, the robotic arm 30, the user interface 40, the robotic controller 50 and the tracking system 60 can be coupled to a base 70.

The cutting system 100 can include an end effector 20 connection mechanism 116 adapted to couple the cutting system 100 to an end effector 20 of the robotic arm 30.

To enable a cutting operation to be performed, the cutting system 100 can include a cutting element 104 disposed in a housing 106. The cutting element 104 can be populated with a plurality of cutting implements 108 that are arranged to machine a planar surface. Examples of a cutting element 104 having a plurality of cutting implements 108 will be described in FIGS. 2-5 and 9-11. Together, the plurality of cutting implements 108 can form a two-dimensional cutting surface capable of machining a planar bone surface (to receive an implant).

An actuator 102 may be present to move the cutting element 104 disposed in the housing 106, relative to the housing 106 to extend or retract the cutting element 104. In an embodiment, the cutting element 104 may move in a planar direction while the housing 106 is fixed relative to the bone.

In some examples, the entire cutting element 104 can be extended or retracted with respect to the housing 106 by the actuator 102 such that the two-dimensional cutting surface can be selectively exposed outside the housing 106. In other words, the actuator 102 can, but is not required, to move the plurality of cutting implements 108 together. In some examples, the actuator 102 can move at least one of a plurality of cutting implements 108 relative to a housing 106 to extend or retract the at least one of the plurality of cutting implements 108, and/or move the cutting implements in a plane relative to the housing 106, i.e., in a plane to which a direction of extension/retraction is normal.

The cutting system 100 can also include an oscillator 110 to oscillate the cutting element 104. In some examples, the oscillator 110 can oscillate only some of the plurality of cutting implements 108. The oscillator 110 can also oscillate each of the plurality of cutting implements 108 relative to the housing 106, or the plurality of cutting implements 108 can be oscillated together relative to the housing 106. In some examples, the housing 106 can be oscillated together with the cutting element 104.

The cutting system 100 can also include a rotator 112 to rotate the housing 106 and the cutting element 104. In some examples, the rotator 112 can rotate the cutting element 104 (including the plurality of cutting elements 108 together) relative to the housing 106. The rotation action provided by the rotator 112 can be described as providing a second motion component, in addition to any first motion component that is provided to each of the plurality of cutting implements 108.

The cutting system 100 can be controlled by a control system including a cutting control mechanism 114 that is in communication with the robotic controller 50 of the surgical robot 10. The control system 610 is described in further detail in FIG. 6.

Figure 2:
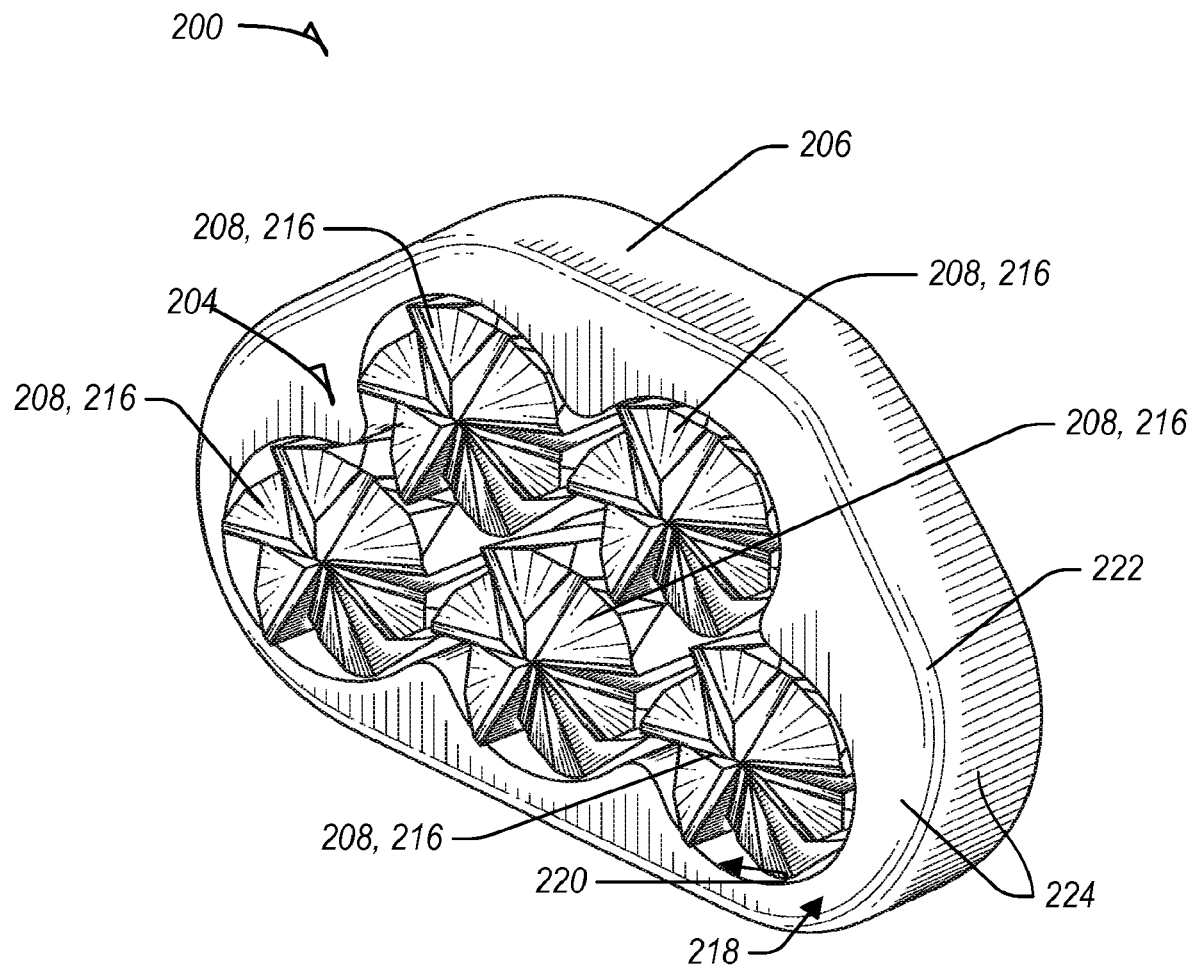
FIG. 2 illustrates a perspective view of an example cutting system that can be used with the surgical robot of FIG. 1, in accordance with at least one example.

FIG. 2 illustrates a perspective view of a portion of an example cutting system 200 that can be used in conjunction with the surgical robot 10 of FIG. 1. In general, the cutting system 200 can be used to prepare a planar bone surface.

A housing 206 can include a superior surface 218 at a distal end portion and an inferior surface 220 opposite the superior surface 218. A perimeter 222 of the distal end portion of the housing 206 can include a shield 224 around a cutting element 204 (e.g., a plurality of cutting implements 208). The shield 224 can protect soft tissue located adjacent to a bone cutting site from inadvertent contact with the plurality of cutting implements 208. The shield 224 may have a contour design or fabricated to be patient specific, for example in the form of a lip. The patient specific shield 224 may be fabricated using pre-operative imaging of the bone, in such a way to be a negative of the bone surface, for the complementary abutment between the shield 224 and the surface of the bone.

In the example of FIG. 2, the housing 206 is shown having a generally trapezoidal perimeter 222 around the plurality of cutting implements 208. The generally trapezoidal perimeter 222 can be shaped to complement the shape of a cross-sectional a bone surfaces to be machined (e.g., femur, tibia). Other perimeter shapes can be provided, including generally triangular, parallelogram, rectangular or irregular shapes. The plurality of cutting implements 208 can be disposed within the housing 206 and can be exposable through the superior surface 218.

The cutting element 204 can be populated with the plurality of cutting implements 208 that are arranged to machine a planar surface. Together, the plurality of cutting implements 208 can form a two-dimensional cutting surface. In some examples, the entire cutting element 204 can be extended or retracted with respect to the housing 206 such that the two-dimensional cutting surface can be exposed outside the housing 206.

The cutting control mechanism 114 (FIG. 1) can be in communication with the robotic controller 50 (FIG. 1) to control operation of the cutting element 204. The cutting control mechanism 114 (FIG. 1) can control the operation of each of the plurality of implements 208 together, or separately.

The cutting control mechanism 114 (FIG. 1) can receive signals from the robotic controller 50 (FIG. 1) to expose or retract the cutting element 204, and therefore the two-dimensional cutting surface, outside of the housing 206. The cutting control mechanism 114 (FIG. 1) can also activate or deactivate the entire cutting element 204, or the individual plurality of cutting implements 208 individually, based on signals from the robotic controller 50 (FIG. 1). The activation and/or deactivation of all or some of the cutting implements 208 (or all other cutting implements described herein), along with other control features such as the deceleration of the cutting implements 208, may be performed to avoid removing bone that it is desired to preserve. Stated differently, some selective disabling of cutting implements may be controlled to avoid certain bone, such as bone in a no-cut zone.

As shown in the example of FIG. 2, the plurality of cutting implements 208 can include a plurality of cutting mills 216 disposed in a pattern (e.g., array). To perform a milling operation, each of the plurality of cutting mills 216 can be rotated respectively upon activation of the cutting element 204, about axes R. In an embodiment, all axes R are parallel to one another, and normal to a resulting two-dimensional cutting surface (a.k.a., cutting plane) on the bone. The rotational motion of each of the plurality of cutting mills 216 can be described as a first motion component delivered to the cutting element 204. In another example, instead of the first motion component being rotational, each cutting mill 216 of the plurality of cutting mills 216 can oscillate upon activation of the cutting element 204 (e.g., each of the plurality of cutting mills may not fully rotate, but rather can oscillate about axes R).

The plurality of cutting mills 216 be arranged and controlled to cooperate with each other such that together the plurality of cutting mills 216 are capable of machining a planar bone surface.

To facilitate cutting a planar bone surface with the plurality of cutting mills 216, the cutting system 200 can include a structure to oscillate or rotate the cutting element 204. The cutting element 204 can be oscillated or rotated together as a whole. The oscillation or rotation of the cutting element 204 (e.g., as a whole) can be in addition to rotational or oscillating movement provided to each of the plurality of cutting mills 216. By oscillating or rotating the cutting element 204 as a whole, the plurality of cutting mills 216 can machine the bone tissue located in between the plurality of cutting mills 216 during a surgical procedure. This oscillating or rotating movement of the cutting element 204 as a whole can enable the cutting system 200 to form a two-dimensional cutting surface. The two-dimensional cutting surface can thus be capable of milling a planar bone surface. The cutting element 204 can also be translated along the bone surface to create the planar bone surface, namely move along axis X and/or axis Y.

Figure 3:
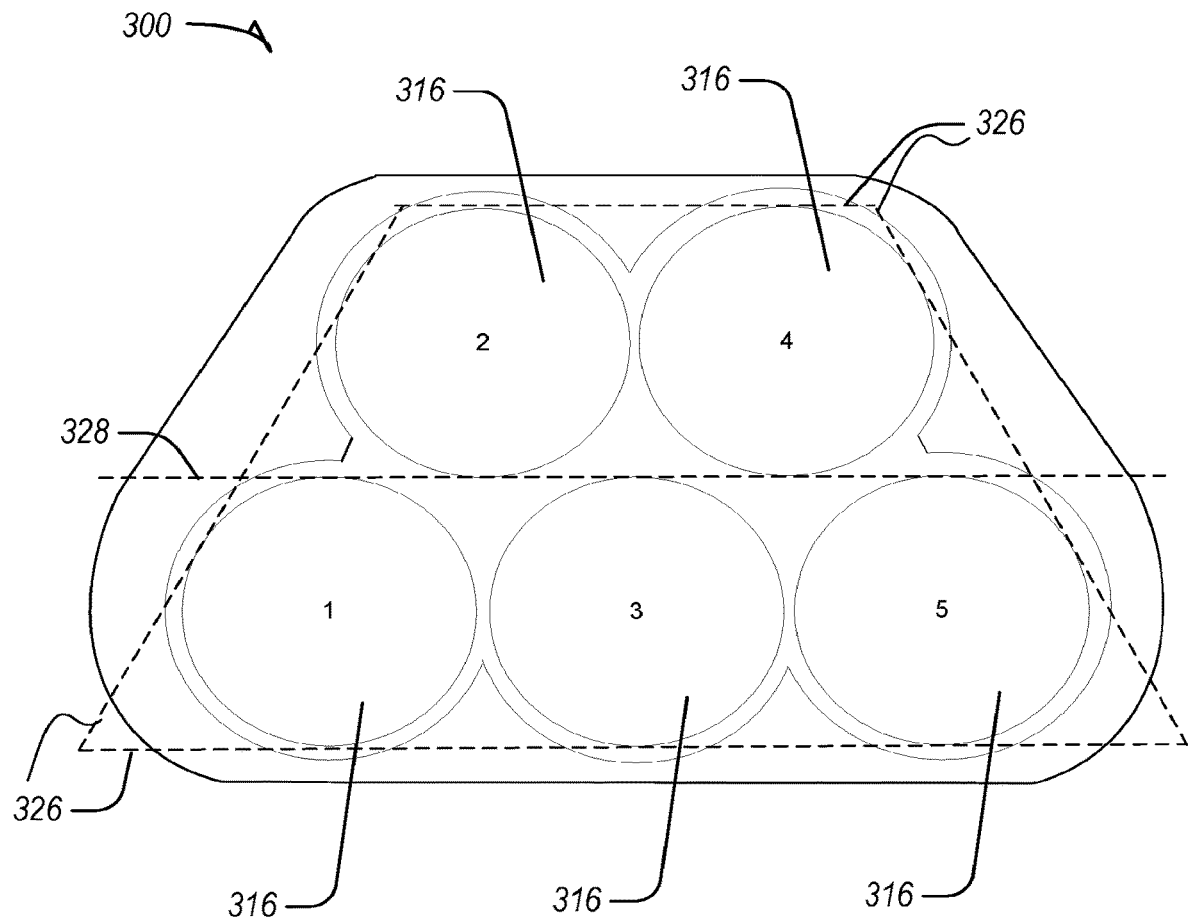
FIG. 3 illustrates a plan view schematic showing an example geometry of the cutting system of FIG. 2, in accordance with at least one example.

FIG. 3 illustrates a plan view schematic showing an example geometry 300 of the cutting system 200 of FIG. 2. In the example shown, a plurality of cutting mills 316 can include five cutting mills 316 positioned in a trapezoidal arrangement. A trapezoidal arrangement can be described as occurring when lines 326 tangent to outer radii of the cutting mills 316 generally form a trapezoid. A trapezoidal arrangement can also be described as occurring when lines from center to center of the cutting mills 316 (i.e., at axes R) form a trapezoid.

In some examples, the plurality of cutting implements can be some number other than the five cutting mills 316 shown in FIG. 3. For example, three cutting mills positioned in a triangular arrangement may be provided. A triangular arrangement can be described similarly to the trapezoidal arrangement (e.g., lines tangent to outer radii of the cutting mills form a triangle). A single cutting mill may also be present, and may move along axis X and/or axis Y.

In some examples, the plurality of cutting mills include four cutting mills positioned in a generally parallelogram arrangement or in a rectangular arrangement. In other words, a parallelogram arrangement can be described as lines tangent to outer radii of the cutting mills form a parallelogram. A rectangular or parallelogram arrangement can also be described as occurring when lines from center to center of the cutting mills 316 (i.e., at axes R) form a rectangle or a parallelogram.

Figure 4:
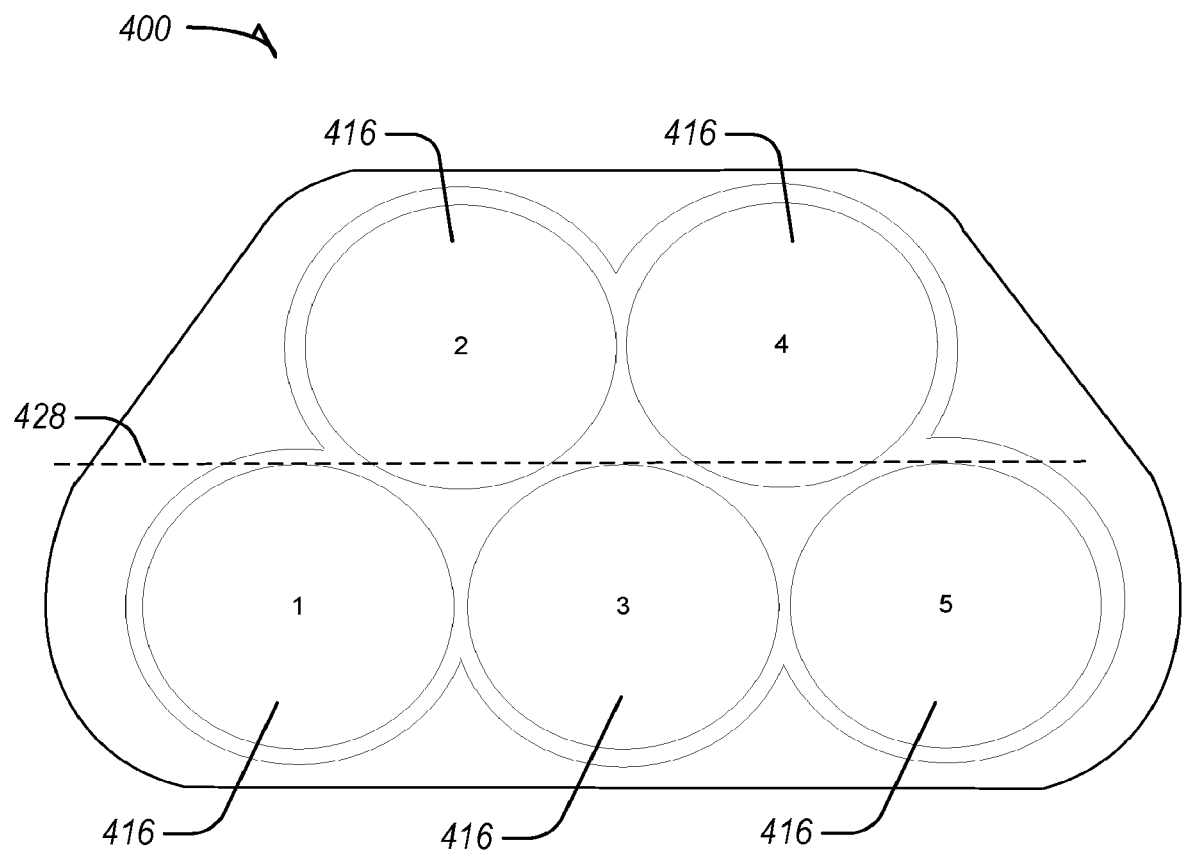
FIG. 4 illustrates a plan view schematic of another example geometry of the cutting system of FIG. 2, in accordance with at least one example.
Figure 5:
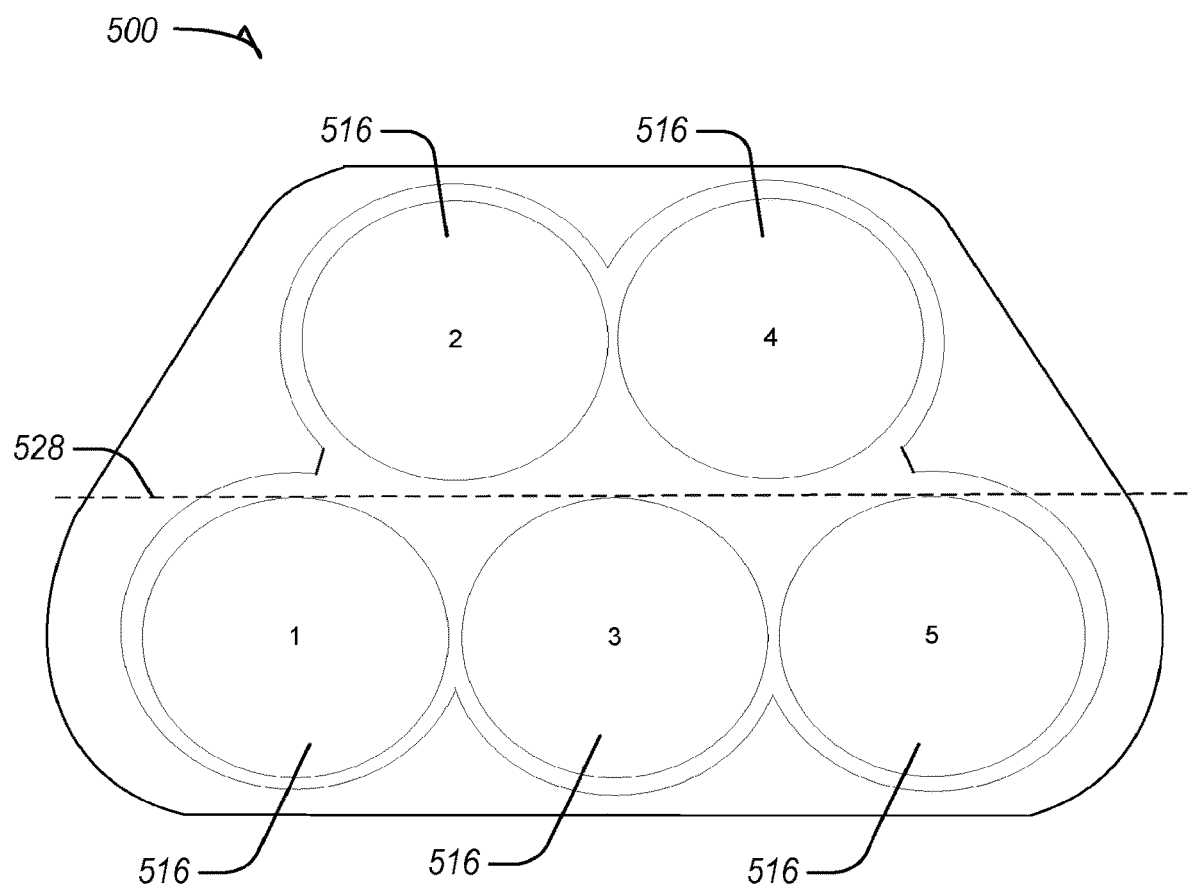
FIG. 5 illustrates a plan view schematic of another example geometry of the cutting system of FIG. 2, in accordance with at least one example.

Another way of describing the location of the plurality of cutting mills 216 relative to each other is shown in the examples of FIGS. 3-5. The plurality of cutting mills 316 (FIG. 3), 416 (FIG. 4), 516 (FIG. 5) can include a first cutting mill 1, a second cutting mill 2, a third cutting mill 3, a fourth cutting mill 4 and a fifth cutting mill 5.

As shown in FIGS. 3-5, the first, third and fifth cutting mills 1, 3, 5 can be located adjacent to one another, and the second and fourth cutting mills 2 may be staggered with respect to the first, third and fifth cutting mills 1, 3, 5. This arrangement of the implements may be described as a staggered or zig-zag type arrangement.

As shown in the geometry of FIG. 3, in some examples, an axis 328 extending tangent from the first cutting mill 1 to the third cutting mill 3 can be tangential to the second cutting mill 2. Likewise, the axis 328 can also extend tangent from the third cutting mill 3 to the fifth cutting mill 5 and can be tangential to the fourth cutting mill 4.

As shown in the geometry of FIG. 4, in some examples, an axis 428 extending tangent from the first cutting mill 1 to the third cutting mill 3 can intersect the second cutting mill 2. Likewise, the axis 428 can also extend tangent from the third cutting mill 3 to the fifth cutting mill 5 and can intersect the fourth cutting mill 4.

As shown in the geometry of FIG. 5, in some examples, the axis 528 extending tangent from the first cutting mill 1 to the third and fifth cutting mills 3, 5 may not necessarily intersect the second or fourth cutting mills 2, 4. Instead, the first third and fifth mills 3, 5 can be spaced apart from the second and fourth mills 2, 4. As shown in FIG. 5, the first, third and fifth cutting mills 1, 3, 5 can be located below the axis 528, and the second and fourth cutting mills 2, 4 can be located above the axis 528.

Figure 12:
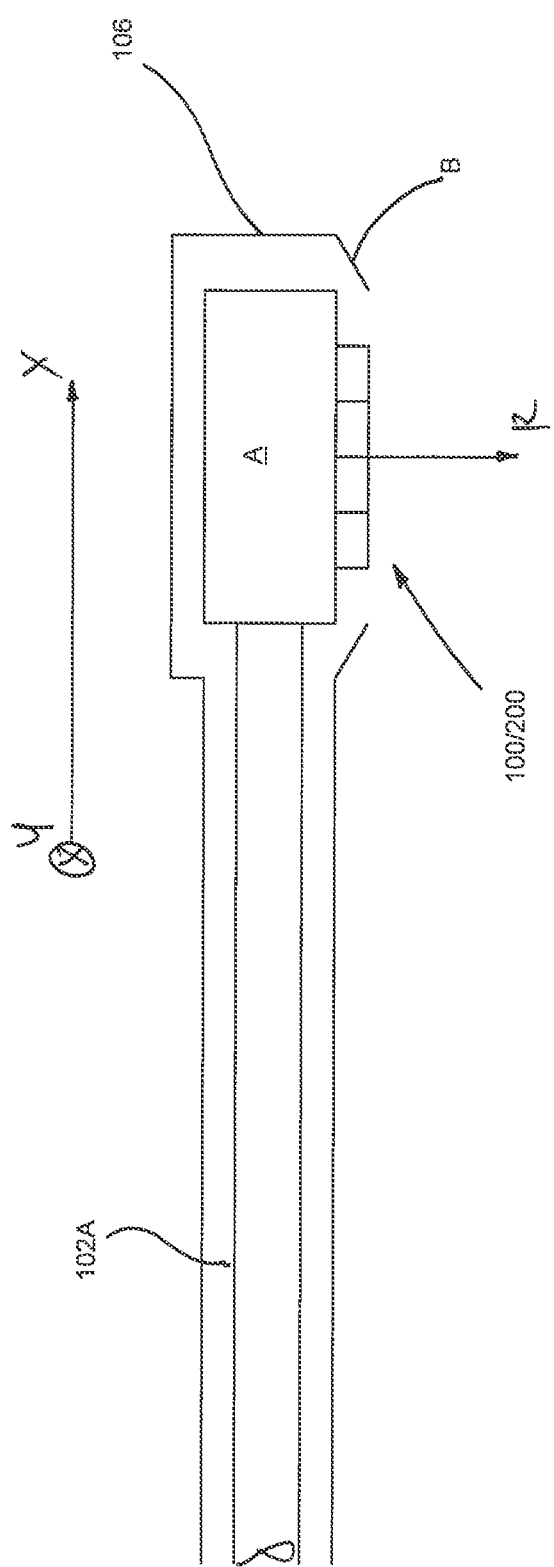
FIG. 12 illustrates a schematic sectional view of examples relative movements of cutting system relative to rotational axes and to a housing.

The various cutting implements described above, such as 108, 216, 316, 416 and 518 may be driven in any appropriate way. As shown in FIG. 12, it may be desired to move these cutting implements in a X,Y plane to which rotational axes R are normal, or along directions X or Y. The cutting implements may have their own motors, or may have a transmission. The transmission may include an endless worm and gears, tendons and pulleys, chains and sprocket. For example, the actuator 102 may include a shaft 102A that is oriented transversely relative to the rotational axes R, and connected thereto by a transmission A. This may allow the maneuvering of the cutting systems 100 and 200 from a lateral approach, as opposed to displacing the cutting systems 100 and 200 along a direction parallel to axes R. To assist in keeping the cutting system 100 and 200 fixed relative to the bone, clamps or temporary fasteners B may be used.

Figure 6:
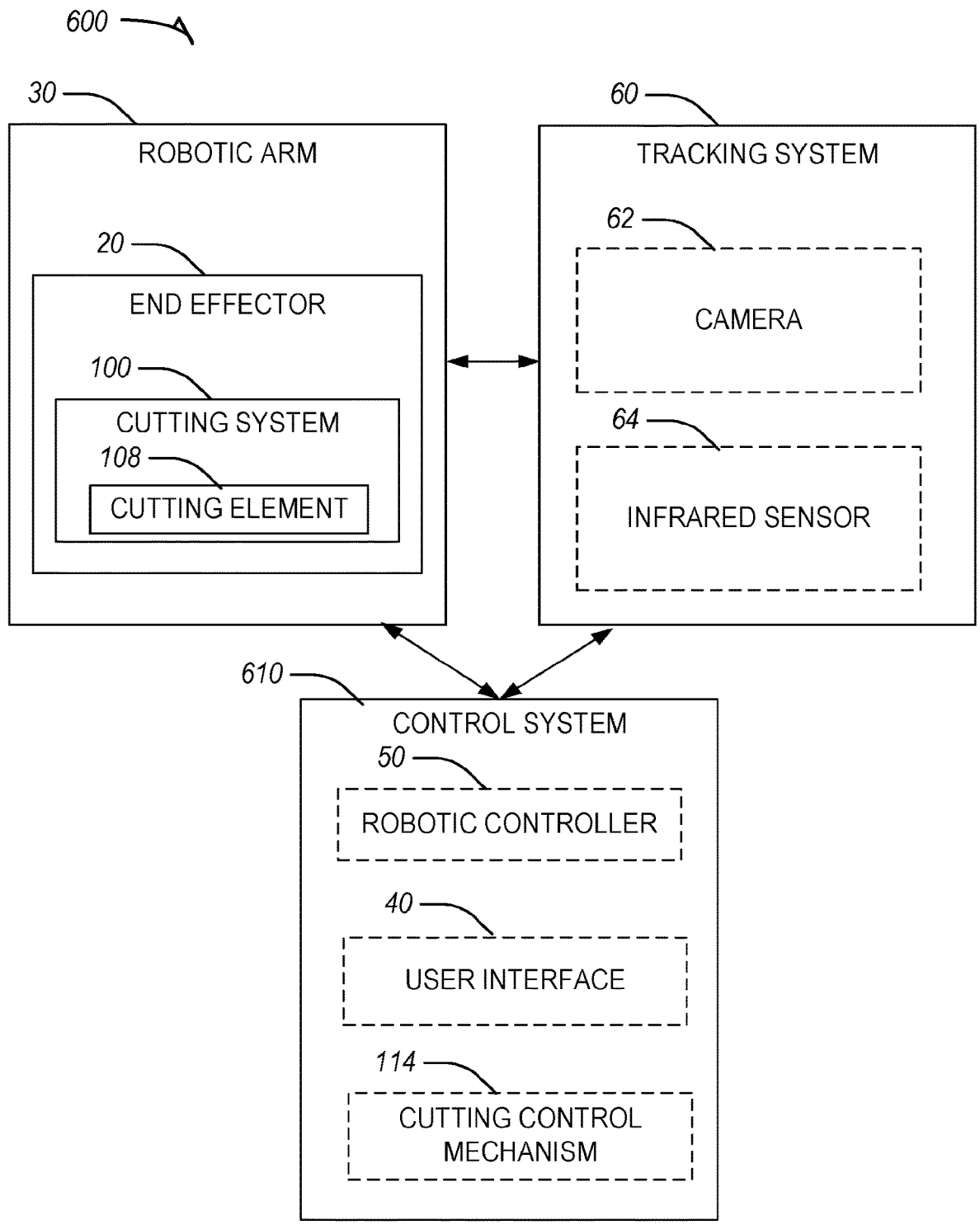
FIG. 6 illustrates a system for performing a surgical procedure including tracking and control, in accordance with at least one example.

FIG. 6 illustrates a system 600 for performing a surgical procedure including tracking and control in accordance with some embodiments. The system 600 will be described with respect to the surgical robot 10 and cutting system 100 shown in FIG. 1, but the system 600 can also be used with other surgical robots and cutting systems.

The system 600 can include a robotic arm 30 including an end effector 20, a tracking system 60, and a control system 50. The system 600 can also include a cutting system 100 having a cutting element 104. The robotic arm 30 can be configured to allow interactive movement and controlled autonomous movement of the end effector 20. The system 600 can be configured to control the cutting element 104 to machine a planar surface.

The tracking system 60 can include a camera 62 or an infrared sensor 64. The tracking system 60 can use the camera 62 or the infrared sensor 64 to track the robotic arm 30, the end effector 20, the cutting element 104, a target object, or the like. In an example, the tracking system 60 can be used to determine a position and/or an orientation of the cutting element 104. The position or the orientation can be determined relative to a coordinate system or relative to a target object. In an embodiment, the bones and end effector 20 are in a common three-axis coordinate system. An example optical tracking device commonly used for this type of application is the Polaris Optical Tracking System from Northern Digital of Waterloo, Ontario, Canada. The camera 62 may for example be a three-dimensional (3D) camera having two points of view to provide positional readings for objects in a 3D coordinate system. For example, the camera 62 may track retro-reflective trackers, such as shown at 60' in FIG. 1. While only one such tracker 60' is shown in FIG. 1, the tracking system 60 may have additional trackers 60', such as one on the robotic arm 30 (e.g., in proximity to the end effector 20 or on the end effector 20 or cutting system 100), and/or one or more on the bone(s) underdoing resurfacing surgery. In an embodiment, a tracker has three or more reflective elements, arranged in a unique geometry. The tracking system 60 may further be programmed with geometrical data to correlate the trackers 60' with the objects they are on. Using the geometrical data, the tracking system 60 can determine a position and/or orientation of the cutting elements 108 relative to the coordinate system and relative to the bone. This tracking system 60 may further include encoders in the joints of the robotic arm 30, for the tracking system 60 to determine the position of the end effector 20 relative to the coordinate system by encoder data. This tracking via encoders may, in an embodiment, be used as redundant tracking to ensure the accuracy of the optical tracking described above.

The control system 610 can include a user interface 40. In another example, the user interface 40 can be separate from the control system 610 or can be communicatively coupled to the control system 610. The user interface 40 may include one or more of a monitor, a mouse, a touchscreen, and/or tablet or like handheld unit.

In some examples, the control system 610 can control aspects of the cutting system 100, based on a tracked position of the cutting element 104 relative to a coordinate system. To determine position and orientation of the cutting element 104 during a surgical procedure, the tracking system 60 can be used in conjunction with the control system 610 to control position, orientation and a cutting process. The control system 610 may control the robotic arm 30 in its 3D working volume. In an embodiment, the robotic arm 30 is a serial arm with the end effector 20 movable in at least 6 degrees of freedom (DOF) relative to the surgical table. This may include 3 rotational DOFs and 3 translational DOFs. The control system 610 may therefore control the various joints to control the position and/or orientation of the end effector 20 in the coordinate system of surgery.

Another of the components that the control system 610 can control is the actuator 102 (FIG. 1). Based on signals received from the robotic controller 50, the cutting control mechanism 114 can cause the actuator 102 (FIG. 1) to extend or retract at least one of the plurality of cutting implements 108 into and out of the housing 106 (FIG. 1).

The control system 610 can also activate or deactivate at least one of the plurality of cutting implements 108 (FIG. 1) based on the tracked position. In some examples, the control system 610 controls all of the cutting implements 108 (FIG. 1) together (e.g., at the same speed or depth). In other examples, the control system 610 can control each of the plurality of cutting implements 108 independently, or certain functions of the cutting implements 108 (FIG. 1) can be controlled independently. In other words, the rotational speed, retraction, or extension of each of the plurality of cutting implements 108 (FIG. 1) can be separately controlled and adjusted.

The control system 610 can also control a rotational or oscillating speed of at least one of the cutting implements 108 (FIG. 1) based on a tracked position. The control system 610 can control the rotational or oscillating speed of the plurality of cutting implements 108 (FIG. 1) within the housing 106 (FIG. 1). In an example where the housing 106 rotates or oscillates with the cutting implements 108, the control system 610 can control a rotational or oscillating speed of the housing 106 (FIG. 1).

In some examples, the control system 610 can be used to determine a zone occupied by the cutting element 104, such as using the position or the orientation of the cutting element 104, a target object, or a coordinate system. The zone can include a safety zone, an interaction zone, or a free-drive zone. In response to determining the zone is a free-drive zone, the control system 610 can permit interactive movement of the end effector 20 and prevent autonomous movement of the end effector 20. In response to determining the zone is an interactive zone, the control system 610 can permit interactive movement and autonomous movement of the end effector 20.

The control system 610 can prevent movement (autonomous or interactive) into the safety zone. In an example, the control system 610 can, in response to determining that the zone is the interaction zone, cause autonomous movement of the end effector 20 to a cutting position. The autonomous movement can be caused in response to selection of a selectable indication for the movement on the user interface 40. The user interface 40 can be used to select a predetermined cutting position, such as a position and/or orientation relative to the target object. In an example, the control system 610 can disable the selectable indication in response to determining the zone is a free-drive zone. In an example, the control system 610 can activate the selectable indication in response to determining that the zone is the interaction zone.

After moving the end effector 20 to the cutting position, the cutting element 104 can be allowed to move interactively along a cutting surface. The cutting element 104 can be prevented from moving outside of a cut plane or cut line by the control system 610. In an example, the cutting element 104 can be permitted to enter the safety zone by the control system 610 while the cutting element 104 is in the cut plane or cut line. This permission can occur, in an example, only after autonomous movement of the cutting element 104 to the cutting position.

In an example, the tracking system 60 can determine a trajectory of the cutting element 104, such as from an interactive force applied to the cutting element 104 or a portion of the cutting element 104, the end effector 20, or the robotic arm 30. The control system 610 can determine that the trajectory would cause the robotic arm 30 or a portion of the robotic arm, the end effector 20, or the cutting element 104 to enter the safety zone. In response to determining that the trajectory would cause entry into the safety zone, the control system 610 can prevent movement of the robotic arm 30.

In an example, the control system 610 can establish the interaction zone using anatomical landmarks of the target object (e.g., a target bone) or identified locations of the target object (e.g., digitized locations). The tracking system 60 can determine a position or an orientation of a target object relative to the coordinate system. The position or the orientation of the cutting element 104 can be determined relative to the position or the orientation of the target object by the tracking system 60. In an example, the coordinate system is determined from the position or the orientation of the target object. The activation and/or deactivation of all or some of the cutting implements, along with other control features such as the deceleration of the cutting implements, may be performed by the control system 610 to avoid removing bone that it is desired to preserve. Stated differently, some selective disabling of cutting implements may be controlled to avoid certain bone, such as bone in a no-cut zone).

In some examples, the control system 610 can identify or determine if a portion of the bone to be removed was missed and to cause the cutting system 100 to return to that portion and remove it.

Figure 7:
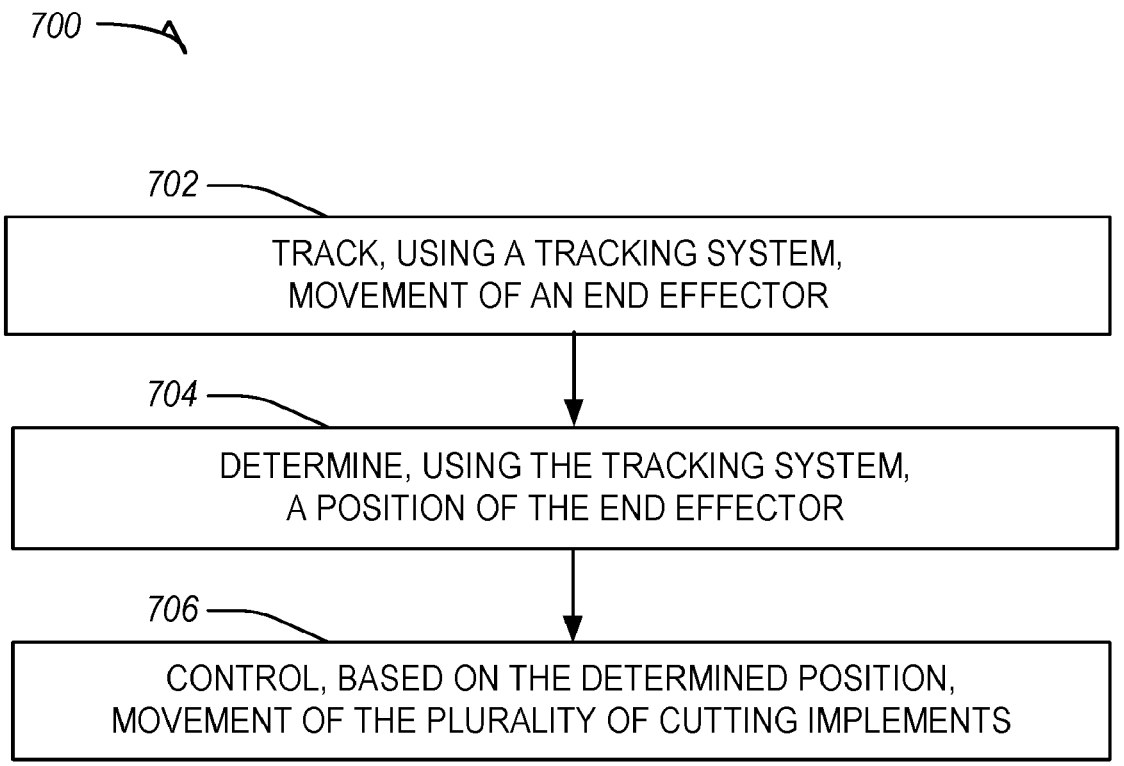
FIG. 7 illustrates a flowchart showing a technique for performing a surgical procedure using a cutting system attached to an end effector of a surgical robot, in accordance with at least one example.

FIG. 7 shows a flow chart illustrating a technique for preparing a bone surface. The technique 700 can be used with the cutting systems 100, 200, 300, 400, 500, 600, 900 and 1000 described in FIGS. 1-6 and 9-11, but can also be used with other cutting systems. Alternatively, the cutting systems 100, 200, 300, 400, 500, 600, 900 and 1000 can also be used with other techniques.

In technique 700, operation 702 can include to track, using a tracking system, movement of an end effector of a robotic arm. A cutting system can be coupled to the end effector, for example, as shown and described in at least FIGS. 1-6. The cutting system can include a housing and a plurality of cutting implements disposed in the housing. The housing can have a superior surface and an inferior surface. The cutting implements can be positioned in an (pattern (e.g., array) within the housing. Operation 702 may be performed continuously during technique 700 (even through subsequent operations such as 704 and 706), or continuous during given intervals in which the relative positioning is required. Operation 702 may be performed in realtime.

In technique 700, operation 704 can include to determine, using the tracking system, a position of the end effector. Operation 704 may be performed continuously during technique 700, or continuous during given intervals in which the relative positioning is required. Operation 704, once have begun, may be performed simultaneously with operation 702. Operation 704 may be performed in realtime.

In technique 700, operation 706 can include to control, based on the determined position in operation 704, the movement of the plurality of cutting implements. In the example where the plurality of cutting implements are cutting mills, each cutting mill can be rotated or oscillated, as well as the plurality of mills being rotated, oscillated or translated together as one cutting element in a combined motion. For example, the operation 706 may be done at selected times while the operations 702 and 704 are continuous.

In technique 700, operation 706 can include controlling the movement of the plurality of cutting implements to machine a planar surface on bone tissue. Suitable applications for machining a planar surface include knee arthroplasties, including total knee arthroplasties.

Controlling the cutting system in operation 706 can include actuating, based on the determined position in operation 704, an actuator to extend and retract at least one of the plurality of cutting implements into and out of the superior surface of the housing, and/or translate the cutting elements relative to a housing.

In technique 700, operation 706 can also include to activate or deactivate, based on the determined position, at least one of the plurality of cutting implements. In some examples, all of the plurality of cutting implements can be activated or deactivated together.

In technique 700, operation 706 can also include to move the cutting implements to produce the planar surface. In some examples, moving the cutting implements can include moving the housing together with or separate from the cutting elements.

In some examples, moving the cutting implements can include a combination of movements. For example, operation 706 can include rotating, oscillating or translating each cutting implement. In some examples, operation 706 can also include inducing a second motion to the array of cutting implements to move the cutting elements together. This second motion can be applied to just the plurality of cutting elements, or the second motion can be applied to the housing and the cutting implements together.

In other words, in the example of FIGS. 1-5 where the cutting implements are shown as mills, in addition to each mill being rotated or oscillated to perform the milling operation, a second motion can be provided to oscillate, rotate or translate the array of cutting implements collectively. The combination of motions (e.g., compound motion) can facilitate machining the bone tissue located in the gap(s) between the cutting implements.

In some examples, moving the cutting implements can include to adjust, based on the determined position, a rotation or oscillation speed of at least one of the plurality of cutting implements. The rotation or oscillation speed of the plurality of cutting implements maybe controlled and adjusted so that the speed of each cutting implement is the same, or, the speed of individual cutting elements can be individually controlled and adjusted. Individual adjustment can be used to provide more customized machining. For example, if bone tissue across the surface has different characteristics (density, brittleness, quality, etc.), the machine control can be adjusted locally at each of the plurality of cutting implements.

Figure 8:
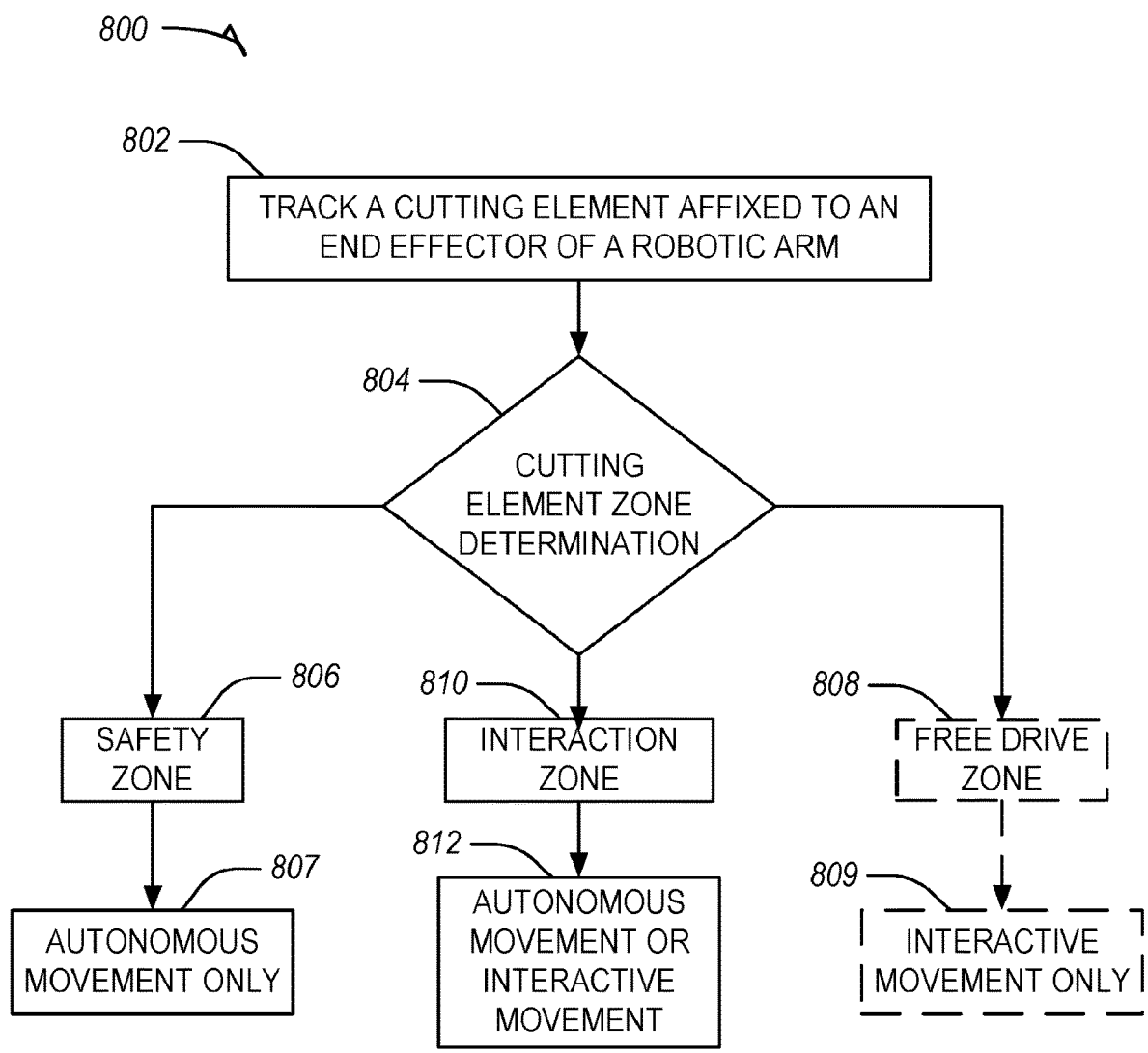
FIG. 8 illustrates a flow chart showing a technique for surgical tracking and control, in accordance with at least one example.

FIG. 8 illustrates a flowchart showing a technique for 800 performing a surgical procedure including controlling a cutting system in accordance with some embodiments. As with technique 700, the technique 800 can also be used with the cutting systems 100, 200, 300, 400, 500, 600, 900 and 1000 described herein, but can also be used with other cutting systems. Alternatively, the cutting systems 100, 200, 300, 400, 500, 600, 900 and 1000 described herein can also be used with other methods.

The control system (e.g. 610, FIG. 6) can be adapted to determine a cut zone and a no-cut zone. Using the determined cut zones, the control system can control position, orientation and a cutting process of the cutting tool to permit cutting in the cut zone and to prevent cutting in the no-cut zone.

The control system can determine and establish the cut zone using anatomical landmarks of a target bone. In some examples, the cutting element can be allowed to enter a safety zone while in the cut plane.

The technique 800 can include an operation 802 to track a cutting system affixed to an end effector of a robotic arm. The cutting system can include a plurality of cutting implements disposed in a housing. Operation 802 may be performed continuously during technique 800 (even through subsequent operations such as 804), or continuous during given intervals in which the relative positioning is required. Operation 802 may be performed in realtime.

The technique 800 can include a decision operation 804 to perform a zone determination. In an example, the decision operation 804 can be performed using a tracking system. For example, a tracking system can be used to track an end effector of a robotic cutting system (e.g., using a robotic controller) and a position or positions of a bone or other patient anatomy (e.g., using an optical tracker). The tracking system can determine where the end effector is relative to aspects of patient anatomy or absolute positions of either or both the end effector and the patient anatomy. When the determination indicates the zone is a safety zone 806, the technique 800 can include an operation 807 to allow autonomous movement only. For example, the robotic arm can resist any movement other than autonomous movement controlled by a robotic controller. An intentional or accidental force, such as by a surgeon, can be resisted or prevented by the robotic arm (e.g., using a counter force initiated by a robotic controller or by simply not enabling movement of any robotic joints). In certain examples, the robotic arm can only be moved through commanded movements. In these examples, the commanded movements can be autonomous or interactive. Within the safety zone the controller can limit commanded movements to only include autonomous movements.

When the determination indicates that the zone is a free drive zone 808, the technique 800 can include an operation 809 to allow interactive movement only (e.g., prevent the robotic arm from moving autonomously or shutting off power or control to the robotic arm). In an example, interactive movement can include force applied by the robotic arm, for example in response to an external force (e.g., by a surgeon) on the arm, as a force assist, but cannot include autonomous (e.g., without the external force) movement.

When the determination indicates the zone is an interaction zone 810, the technique 800 can include an operation 812 to allow autonomous movement or interactive movement. For example, when an end effector at a distal end portion of a robotic arm is in the interaction zone 810, movement can be controlled by a robotic controller or a surgeon manipulating the robotic arm.

The technique 800 can include an operation 814 to autonomously move the end effector such that a plurality of implements can be rotated, oscillated or translated to prepare a planar bone surface. Operation 814 can be performed in response to determining that the cutting element has been moved into the interaction zone. In an example, the interaction zone can be a zone where the surgical instrument can perform a machining step, such as a bone preparation step in a knee arthroplasty. The technique 800 can include an operation 816 to determine that the bone preparation step has been completed.

The technique 800 can include an operation 818 to autonomously move the end effector. In an example, the technique 800 may include determining that a bone surface preparation has been completed, and moving the end effector to the free drive zone 808 or the interaction zone 810. In an example, operations 814, 816, and 818 can be initiated only when the robot is within the interaction zone 810, but can actually take place within the safety zone 806.

The end effector can be autonomously moved (e.g., by the robotic arm controlled by a robotic controller), for example in response to determining that the bone preparation has been completed. The robotic arm may also have a collaborative mode in which a human operator may displace the robotic arm. The collaborative mode may be for non-precise large range maneuvers, such as moving the robotic arm away from the operation site upon completion of the surgery.

Figure 9A:
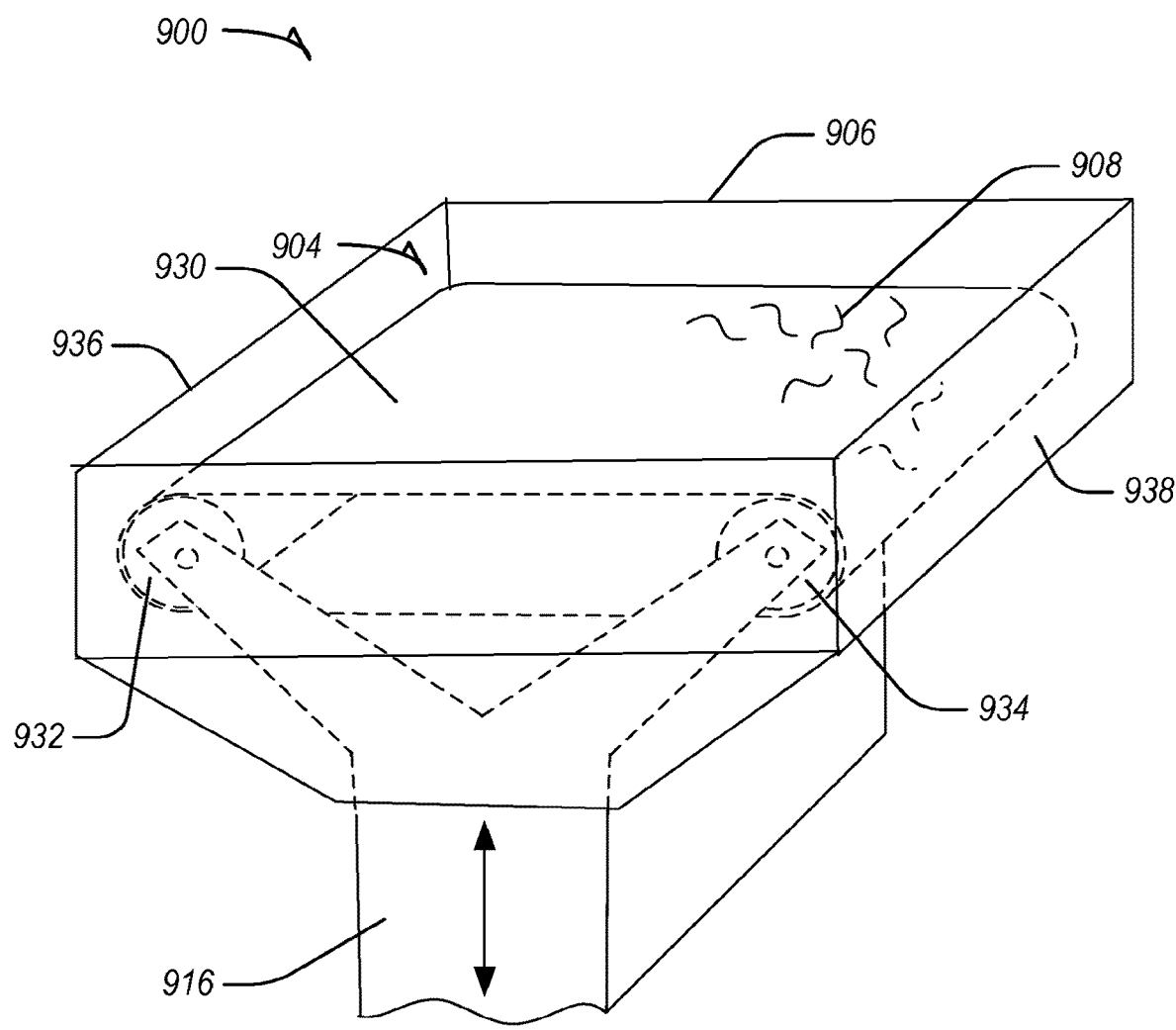
FIG. 9A illustrates a perspective view of another example cutting system having cutting implements that can be used with the surgical robot of FIG. 1, in accordance with at least one example.
Figure 9B:
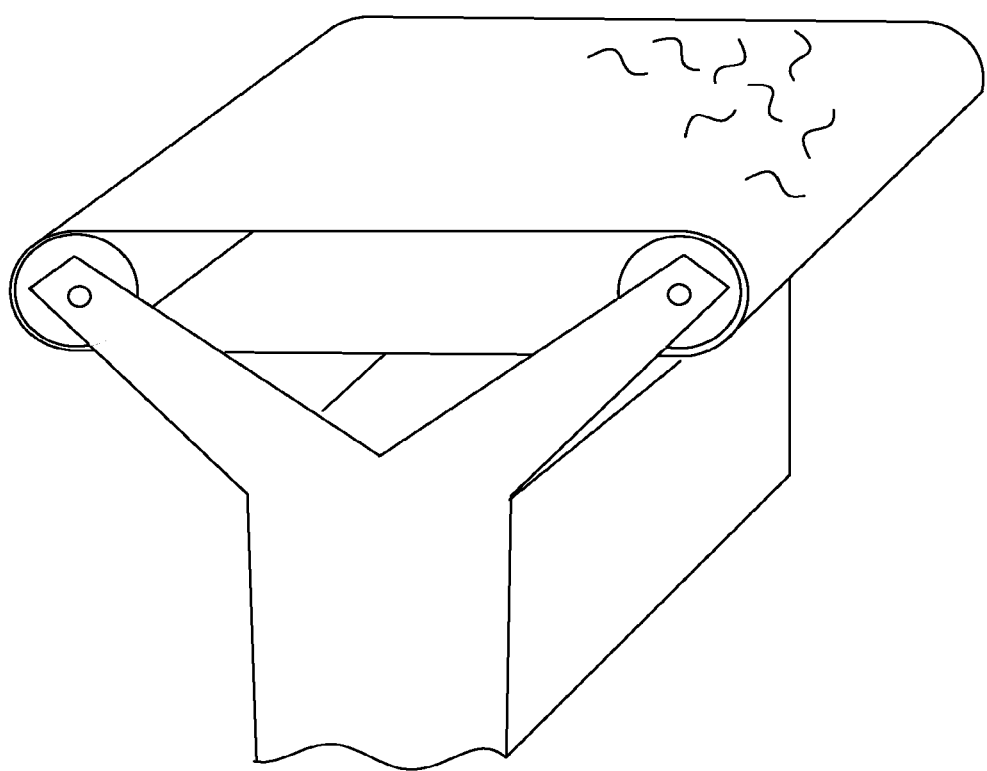
FIG. 9B illustrates a perspective view of the cutting system of FIG. 9A with a housing removed, in accordance with at least one example.

FIG. 9A illustrates a perspective view of another example cutting system 900 having cutting implements 908 that can be used with the surgical robot 10 of FIG. 1, in accordance with at least one example. FIG. 9B illustrates a perspective view of the cutting system 900 of FIG. 9A with a housing 906 shown in FIG. 9A removed.

Figure 10:
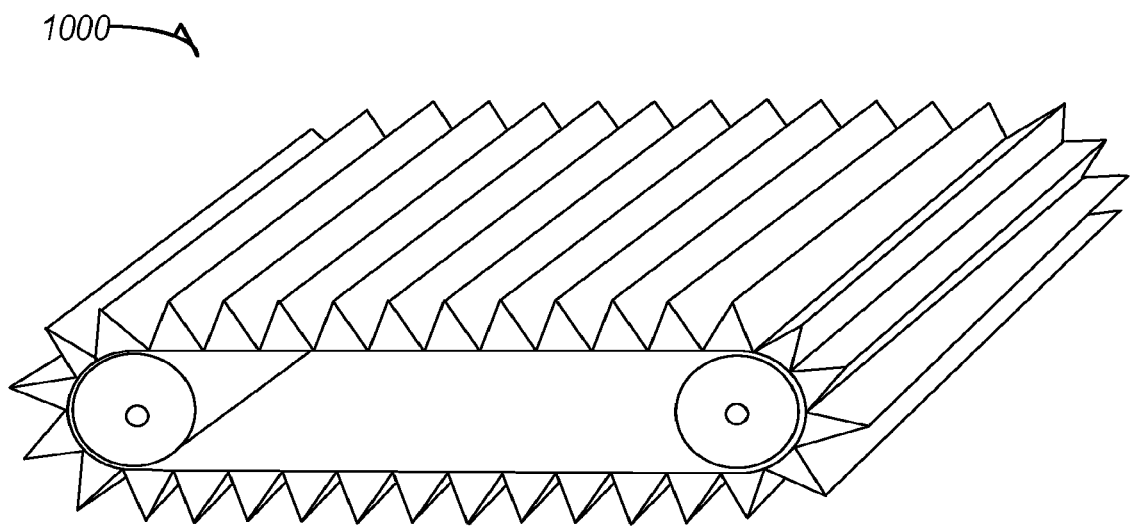
FIG. 10 illustrates a perspective view of a portion of the cutting system of FIG. 9A showing another example of cutting implements, in accordance with at least one example.
Figure 11:
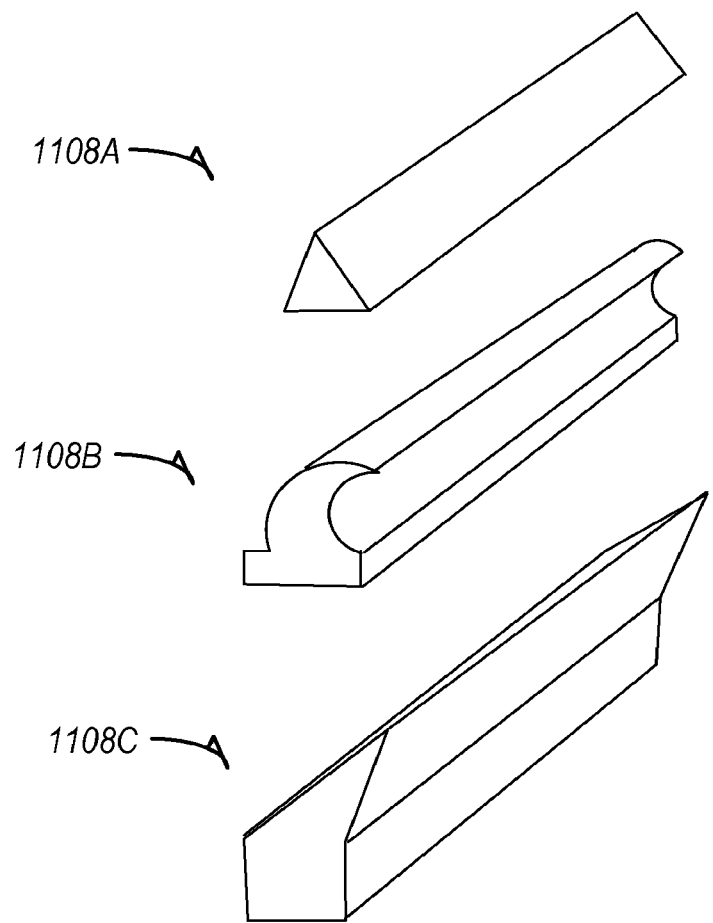
FIG. 11 illustrates a perspective view of examples of cutting implements that can be used in the cutting system of FIG. 10, in accordance with at least one example.

In general, like the cutting system of FIGS. 1-5, the cutting system of FIGS. 9-11 can be used to prepare a planar bone surface, and can employ the features described with respect to FIGS. 1-8.

The cutting system 900 can include a cutting element 904 having a two-dimensional cutting surface including a cutting band 930 (e.g., a flexible cylindrical cutting band).

Like the example of FIG. 1, the cutting system 900 can include an end effector connection mechanism 916 adapted to couple the cutting system 900 to an end effector of a robotic arm (e.g., 30, FIG. 1). The mechanism 916 is shown oriented in a direction that is transverse to the plane of the cutting band 930. It is however considered to orient the mechanism 916 in a parallel or quasi parallel manner relative to the plane of the cutting band 930 (e.g., from −20 degrees to 20 degrees from a parallel relation).

The cutting system 900 can also include a first cylindrical drive member 932 disposed along a first edge 936 (e.g., side) of the housing 906, and a second cylindrical drive member 934 disposed along a second edge 938 (e.g., side) of the housing 906. The cutting band 930 can extend (e.g., be stretched) between the first cylindrical drive member 932 and the second cylindrical drive member 934. The cutting band 930 can form a closed loop (e.g., a flexible eternal band). The cutting band 930 can be rotated upon activation of the cutting element 904 by a rotator (e.g., a motor). In some examples, the rotators can reside inside of the first and/or second cylindrical drive members 932, 934. In some examples, instead of rotating or in addition to rotating the cutting band, the cutting band can be oscillated upon activation of the cutting element 904 by an oscillator (e.g., FIG. 1, 110). The cutting band 930 may also be rotated by way of a transmission. Examples of transmissions include tendons and pulleys, chains and sprockets, gear drives, etc. It is contemplated to use endless worms, etc, for the drive to come from a lateral axis, for instance when the mechanism 916 is in the parallel or quasi parallel arrangement described above.

As shown in FIGS. 9A and 9B, the cutting band 930 can include abrasive elements 908. In some examples, the abrasive elements 908 can be adhered to or molded into the cutting band 930.

FIG. 10 illustrates a perspective view of a portion of the cutting system 900 of FIG. 9 showing another example cutting band 1030, in accordance with at least one example. The cutting band 1030 can be formed from a plurality of cutting implements 1008 joined together as an unending band. Each of the plurality of cutting implements 1008 can be formed as an elongate or linear cutting implement. The plurality of cutting implements 1008 can be joined to each other or to a band of material to form the cutting band 1030. In some examples, the plurality of cutting implements 1008 can be joined to each other by interlocking geometric formations or coupling elements incorporated into the cutting implements 1008. The cutting implements 1080 can be coupled to each other in a flexible manner so the plurality of cutting implements 1008 can bend relative to one another.

FIG. 11 illustrates a perspective view of three example geometries of cutting implements 1108A, 1108B, 1108C that can be used in the cutting system 1000 of FIG. 10, in accordance with at least one example.

In an example, the term "machine readable medium" can include a single medium or multiple media (e.g., a centralized or distributed database, or associated caches and servers) configured to store one or more instructions. The term "machine readable medium" can include any medium that is capable of storing, encoding, or carrying instructions for execution by a machine and that cause the machine to perform any one or more of the techniques of the present disclosure, or that is capable of storing, encoding or carrying data structures used by or associated with such instructions. Non-limiting machine readable medium examples can include solid-state memories, and optical and magnetic media. Specific examples of machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Various Notes & Examples

Each of these non-limiting examples can stand on its own, or can be combined in various permutations or combinations with one or more of the other examples.

Example 1 is a robotically controlled planar cutting system, the planar cutting system comprising: a housing including a superior surface and an inferior surface; a cutting element disposed within the housing, wherein the cutting element is exposable through the superior surface and is populated with a plurality of cutting implements that are arranged to machine a planar surface; a cutting control mechanism in communication with a robotic controller to control the operation of the cutting element to machine the planar surface.

In Example 2, the subject matter of Example 1 includes, wherein the cutting control mechanism receives signals from the robotic controller to expose the two-dimensional cutting surface outside the housing.

In Example 3, the subject matter of Examples 1-2 includes, wherein the cutting control mechanism activates or deactivates the cutting element based on signals from the robotic controller.

In Example 4, the subject matter of Examples 1-3 includes, and end effector connection mechanism to couple the housing to a robotic arm.

In Example 5, the subject matter of Examples 1-4 includes, an oscillator operably coupled to at least one of the cutting element and the housing to oscillate at least one of the cutting element and the housing.

In Example 6, the subject matter of Examples 1-5 includes, a rotator operably coupled to at least one of the cutting element and the housing to rotate at least one of the cutting element and the housing.

In Example 7, the subject matter of Examples 1-6 includes, wherein the two-dimensional cutting surface includes a plurality of cutting mills disposed in a pattern.

In Example 8, the subject matter of Examples 1-7 includes, wherein the cutting control mechanism receives signals from the robotic controller to expose the two-dimensional cutting surface outside the housing.

In Example 9, the subject matter of Example 8 includes, wherein the system includes a mechanism to oscillate or rotate the array of cutting mills.

In Example 10, the subject matter of Examples 8-9 includes, wherein each cutting mill of the plurality of cutting mills rotates upon activation of the cutting element.

In Example 11, the subject matter of Examples 8-10 includes, wherein each cutting mill of the plurality of cutting mills oscillates upon activation of the cutting element.

In Example 12, the subject matter of Examples 1-11 includes, wherein the two-dimensional cutting surface includes a flexible cylindrical cutting band.

In Example 13, the subject matter of Example 12 includes, wherein the cutting control mechanism receives signals from the robotic controller to expose the two-dimensional cutting surface outside the housing.

In Example 14, the subject matter of Examples 12-13 includes, wherein the cutting element includes a first cylindrical drive member disposed along a first edge of the housing and a second cylindrical drive member disposed along a second edge of the housing opposite the first edge.

In Example 15, the subject matter of Example 14 includes, wherein the flexible cylindrical cutting band is stretched between the first cylindrical drive member and the second cylindrical drive member.

In Example 16, the subject matter of Example 15 includes, wherein the flexible cylindrical cutting band rotates upon activation of the cutting element.

In Example 17, the subject matter of Examples 15-16 includes, wherein the flexible cylindrical cutting band oscillates upon activation of the cutting element.

Example 18 is a robotically controlled planar cutting system, the planar cutting system comprising: a housing including a superior surface and an inferior surface; a cutting element having a plurality of cutting implements disposed in the housing, wherein the plurality of cutting implements are arranged in an array; an end effector connection mechanism to couple the housing to a robotic arm; and a cutting control mechanism in communication with a robotic controller to control the operation of the cutting implements to machine a planar surface.

In Example 19, the subject matter of Example 18 includes, wherein the plurality of cutting implements are arranged and controlled to cooperate, such that together the plurality of cutting implements machine the planar surface.

In Example 20, the subject matter of Examples 18-19 includes, wherein the plurality of cutting implements includes at least three cutting mills positioned in a triangular arrangement such that lines tangent to outer radii of the at least three cutting mills form a triangle.

In Example 21, the subject matter of Examples 18-20 includes, wherein the plurality of cutting implements includes at least four cutting mills positioned in a parallelogram arrangement such that lines tangent to outer radii of the at least four cutting mills form a parallelogram.

In Example 22, the subject matter of Examples 18-21 includes, wherein the plurality of cutting implements are positioned in a trapezoidal arrangement such that lines tangent to outer radii of the plurality of cutting mills form a trapezoid.

In Example 23, the subject matter of Examples 18-22 includes, wherein the plurality of cutting implements includes a first cutting implement, a second cutting implement and a third cutting implement, and wherein an axis extending tangent from the first cutting implement to the third cutting implement intersects a portion of the second cutting implement.

In Example 24, the subject matter of Examples 18-23 includes, wherein the plurality of cutting implements includes a first cutting implement, a second cutting implement and a third cutting implement, and wherein an axis extends tangent to the first cutting element, the second cutting element and the third cutting implement.

In Example 25, the subject matter of Examples 18-24 includes, wherein a perimeter of a distal end portion of the housing includes a shield around the plurality of cutting implements to protect soft tissue adjacent to a bone cutting site.

In Example 26, the subject matter of Examples 18-25 includes, wherein the housing includes a generally trapezoidal perimeter around the plurality of cutting implements to protect soft tissue surrounding a bone cutting site.

In Example 27, the subject matter of Examples 18-26 includes, an actuator to move at least one of the plurality of cutting implements relative to the housing to retract or extend the at least one cutting implement thereby preventing or enabling a cutting operation to be performed.

In Example 28, the subject matter of Examples 18-27 includes, an oscillator to oscillate at least one of the plurality of cutting implements and the housing.

In Example 29, the subject matter of Examples 18-28 includes, a rotator to rotate at least one of the plurality of cutting implements.

In Example 30, the subject matter of Examples 18-29 includes, a tracking system to determine a position and an orientation of the cutting element relative to a coordinate system; and a control system to control position, orientation and a cutting process of the cutting tool.

In Example 31, the subject matter of Example 30 includes, wherein the control system controls an actuator to extend and retract at least one of the plurality of cutting implements into and out of the housing based on a tracked position.

In Example 32, the subject matter of Examples 30-31 includes, wherein the control system activates or deactivates at least one of the cutting implements based on a tracked position.

In Example 33, the subject matter of Examples 30-32 includes, wherein the control system controls a rotational or oscillating speed of at least one of the cutting implements based on a tracked position.

In Example 34, the subject matter of Examples 30-33 includes, wherein the control system is adapted to: determine a cut zone; determine a no-cut zone; and control position, orientation and a cutting process of the cutting tool to permit cutting in the cut zone and to prevent cutting in the no-cut zone.

In Example 35, the subject matter of Example 34 includes, wherein the control system is configured to establish the cut zone using anatomical landmarks of a target bone.

In Example 36, the subject matter of Examples 34-35 includes, wherein the cutting element is allowed to enter a safety zone while in the cut plane.

Example 37 is a method for operating a surgical robot, the method comprising: tracking, using a tracking system, movement of an end effector of a robotic arm having a cutting system including a plurality of cutting implements disposed in a housing, wherein the housing has a superior surface and an inferior surface, and wherein the plurality of cutting implements are arranged in an array; determining, using the tracking system, a position of the end effector; and controlling, based on the determined position, movement of the plurality of cutting implements to machine a planar surface.

In Example 38, the subject matter of Example 37 includes, wherein the plurality of cutting implements are arranged in an array.

In Example 39, the subject matter of Examples 37-38 includes, actuating, based on the determined position, an actuator to extend and retract at least one of the plurality of cutting implements into and out of the superior surface of the housing.

In Example 40, the subject matter of Examples 37-39 includes, moving the plurality of cutting implements to remove bone tissue in between the plurality of cutting implements.

In Example 41, the subject matter of Examples 37-40 includes, adjusting, based on the determined position, a rotation or oscillation speed of at least one of the plurality of cutting implements.

Example 42 is at least one non-transitory machine-readable medium including instructions for operation of a robotically controlled surgical planar cutting system, and the instructions, when executed by a processor, cause the processor to perform operations to: track movement of an end effector of a robotic arm, using a tracking system, the robotic arm having a cutting system attached to the end effector, the cutting system including a plurality of cutting implements disposed in a housing, wherein the housing has a superior surface and an inferior surface, and wherein the plurality of cutting implements are arranged in an array; determine a position of the end effector using the tracking system; and control movement of the plurality of cutting implements to machine a planar surface, based on the determined position.

In Example 43, the subject matter of Example 42 includes, to control movement of the plurality of cutting implements includes to control movement of the plurality of cutting implements arranged in an array.

In Example 44, the subject matter of Examples 42-43 includes, to actuate, an actuator to extend and retract at least one of the plurality of cutting implements into and out of the superior surface of the housing, based on the determined position.

In Example 45, the subject matter of Examples 42-44 includes, to move the plurality of cutting implements to remove bone tissue in between the plurality of cutting implements.

In Example 46, the subject matter of Examples 42-45 includes, to adjust a rotation or oscillation speed of at least one of the plurality of cutting implements based on the determined position.

Example 47 is at least one machine-readable medium including instructions that, when executed by processing circuitry, cause the processing circuitry to perform operations to implement of any of Examples 1-46.

Example 48 is an apparatus comprising means to implement of any of Examples 1-46.

Example 49 is a system to implement of any of Examples 1-46.

Example 50 is a method to implement of any of Examples 1-46.

The invention claimed is:

1. A system comprising:
at least one processor;
a non-transitory machine-readable medium including instructions for operation of a robotically controlled surgical planar cutting system, and the instructions, when executed by a processor, cause the processor to perform operations to:
track movement of an end effector of a robotic arm, using a tracking system, the robotic arm having a cutting system attached to the end effector, the cutting system including a plurality of cutting implements disposed in a housing, wherein the housing has a superior surface and an inferior surface, and wherein the plurality of cutting implements are arranged in an array;
determine a position of the end effector using the tracking system; and
control movement of the plurality of cutting implements to machine a planar surface, based on the determined position.

2. The system according to claim 1, wherein to control movement of the plurality of cutting implements includes to control movement of the plurality of cutting implements arranged in an array.

3. The system according to claim 1, including to actuate, an actuator to extend and retract at least one of the plurality of cutting implements into and out of the superior surface of the housing, based on the determined position.

4. The system according to claim 3, wherein to actuate, an actuator to extend and retract at least one of the plurality of cutting implements into and out of the superior surface of the housing includes to displace the at least one cutting implement relative to the housing in a direction parallel to the planar surface.

5. The system according to claim 1, further including to move the plurality of cutting implements to remove bone tissue in between the plurality of cutting implements.

6. The system according to claim 1, further including to adjust a rotation or oscillation speed of at least one of the plurality of cutting implements based on the determined position.

7. The system according to claim 1, further including the robotic arm having the cutting system attached to the end effector, the cutting system including the plurality of cutting implements disposed in the housing, the plurality of cutting implements being arranged in the array.

8. The system according to claim 7, wherein the cutting implements are cutting mills.

9. The system according to claim 8, wherein axes of rotation of the cutting mills are parallel to one another.

10. The system according to claim 7, wherein the robotic arm includes a transmission for the cutting implements having a shaft extending in a direction parallel or quasi-parallel to the planar surface.

11. The system according to claim 7, further including a shield projecting from the superior surface, the shield having a patient-specific contour being a negative of a patient's bone surface.

12. The system according to claim 7, further including at least one clamp adapted to fix the housing to a bone.

13. The system according to claim 1, further including the tracking system.

\* \* \* \* \*